US006958421B2

(12) United States Patent
Bodmann et al.

(10) Patent No.: US 6,958,421 B2
(45) Date of Patent: Oct. 25, 2005

(54) SALT-FREE PREPARATION OF CYCLOBUTANONE

(75) Inventors: Kerstin Bodmann, Marl (DE); Manuela Imig, Marl (DE); Günther Köhler, Marl (DE); Karl-Heinz Brühl, Velen (DE)

(73) Assignee: Degussa AG, Duesseldorf (DE)

( * ) Notice: Subject to any disclaimer, the term of this patent is extended or adjusted under 35 U.S.C. 154(b) by 315 days.

(21) Appl. No.: 10/460,234

(22) Filed: Jun. 13, 2003

(65) Prior Publication Data

US 2004/0254401 A1 Dec. 16, 2004

(51) Int. Cl.[7] ............................................. C07C 45/29
(52) U.S. Cl. ...................... 568/341; 568/342; 568/361
(58) Field of Search ............................... 568/341, 342, 568/361

(56) References Cited

U.S. PATENT DOCUMENTS

| 5,905,176 A | 5/1999 | Liang ........................ 570/214 |
| 6,444,096 B1 * | 9/2002 | Barnicki et al. ............... 203/43 |
| 6,476,274 B1 | 11/2002 | Knops et al. ............... 568/342 |

FOREIGN PATENT DOCUMENTS

DE 199 10 464 9/2000

OTHER PUBLICATIONS

C. C. Lee, et al., Can. J. Chem., vol. 58, pp. 1075-1079, "Reactions of Cyclopropylcarbinol in Dilute Hydrochloric Acid", 1980.

M. Krumpolc, et al., Organic Syntheses, vol. 60, pp. 20-25.

J. Salaün, et al., Organic Syntheses, An Annual Publication of Satisfactory Methods for the Preparation of Organic Chemicals, vol. 64, pp. 50-56, 1986.

K. Mori, et al., Journal of the American Chemical Society, vol. 124, No. 39, XP-002255551, pp. 11572-11573, "Controlled Synthesis of Hydroxyapatite-Supported Palladium Complexes as Highly Efficient Heterogeneous Catalysts", 2002.

A. M.J. Jorna, et al., Reactive & Functional Polymers, vol. 29, XP-002255552, pp. 101-114, "Heterogenization of a Ruthenium Catalyst on Silica and its Application in Alcohol Oxidation and Stilbene Expoxidation", 1996.

Database Crossfire Beilstein 'Online! Beilstein Institur zur Förderung der Chemischen Wissenschaften, AN: Reaction ID 265578, XP-002255553, 1 page.

M. Dojarenko, Chemische Berichte, vol. 1, part B, XP-009018139, pp. 1536-1553, "Isomere Umwandlungen Cyclischer Verbindungen Unter dem Einfluβ Von Katalysatoren, II.: Dehydratation der Alkohole $C_5H_{10}O$: Zersetzung Von Alkoholen $C_4H_8O$ mit $Al_2O_3$ ALS Katalysator[1])", 1927.

* cited by examiner

*Primary Examiner*—Johann Richter
*Assistant Examiner*—Sikarl A. Witherspoon
(74) *Attorney, Agent, or Firm*—Oblon, Spivak, McClelland, Maier & Neustadt, P.C.

(57) ABSTRACT

A salt-free process for preparing cyclobutanone, including isomerizing cyclopropylmethanol, preferably in aqueous solution, in the presence of an acidic heterogeneous catalyst to form cyclobutanol and, preferably after extraction and removal of the extractant, dehydrogenating the cyclobutanol over a heterogeneous catalyst.

20 Claims, No Drawings

SALT-FREE PREPARATION OF CYCLOBUTANONE

BACKGROUND OF THE INVENTION

1. Field of the Invention

The invention relates to a salt-free process for preparing cyclobutanone by isomerizing cyclopropyl-methanol (cyclopropylcarbinol) to cyclobutanol over a heterogeneous acidic catalyst and subsequently catalytically dehydrogenating it to cyclobutanone and the cyclobutanone derived therefrom.

2. Description of the Background

Cyclobutanone is an important and interesting material in organic chemistry, finding use in active ingredients synthesis, for example active pharmaceutical ingredients.

The preparation of cyclobutanone by conversion of cyclopropylmethanol to cyclobutanol and subsequent oxidation is a synthetic route generally known in the literature (Org. Synth. 1981, 60, 20–25).

The isomerization of cyclopropylmethanol to cyclobutanol in the presence of dilute hydrochloric acid is described, for example, in Org. Synth. 1986, 64, 50–56. Only in high dilution (cyclopropylmethanol dilute hydrochloric acid weight ratio=1:12) does the process deliver the desired cyclobutanol. For workup, all of the acid is neutralized and the aqueous phase is additionally saturated with sodium chloride and only then extracted with diethyl ether (yield 57%). From a technical point of view, this process is of little advantage as a consequence of the high salt burden and also the low space-time yield. Furthermore, the use of hydrochloric acid results in chlorinated by-products which are virtually impossible to remove by distillation (Can. J. Chem. 1980, 58(11), 1075–1079) and lead to corrosion and stability problems in the subsequent oxidation step. When using hydrochloric acid of higher concentration, the proportion of chlorinated by-products increases. For example, U.S. Pat. No. 5,905,176 describes the preparation of cyclobutyl chloride by reacting cyclopropylmethanol with 36% hydrochloric acid in the temperature range of 35–120° C.

The processes so far described for the oxidation of cyclobutanol to cyclobutanone use customary oxidizing agents in organic synthesis. A comparison of the existing oxidation methods is given in DE 199 10 464. In general, these are oxidations carried out in homogeneous systems from which the desired cyclobutanone first has to be isolated by extraction or the like. These processes generally lead to large amounts of waste and also to high burdens of toxic reagents, for example when using $CrO_3$/oxalic acid according to Org. Synth. 1981, 60, 20–25. In this process, the direct oxidation of the solution of cyclobutanol in aqueous hydrochloric acid obtained from the isomerization of cyclopropylmethanol is described. For the conversion of 49.5 g of cyclopropylmethanol (results in 14–16 g of cyclobutanone, yield 31–35%), approximately 1.2 l of strongly acidic, chromium-containing wastewater is formed.

DE 199 10 464 likewise describes a one-stage batchwise process for preparing cyclobutanone starting from cyclopropylmethanol by initially isomerizing the cyclopropylmethanol with dilute hydrochloric acid and then oxidizing the aqueous solution obtained with sodium hypochlorite solution. As a consequence of the large amounts of dilute hydrochloric acid and sodium hypochlorite solution required, the process likewise leads to a considerable salt and wastewater burden (according to Example 2, approximately 1,600 g of wastewater for 60 g of cyclobutanone). Moreover, the performance of the oxidation using sodium hypochlorite solution in a strongly acidic medium leads to an increased formation of chlorine which escapes from the reaction mixture in gaseous form. The associated safety and corrosion problems and also the increased formation of chlorinated by-products makes the process relatively unattractive from a technical viewpoint. In addition, storage tests of the cyclobutanone prepared according to the German patent application DE 199 10 464 lead to significant decomposition. Strong coloration of the material is observed within a short time, especially in batches having a high chlorine content.

SUMMARY OF THE INVENTION

Accordingly, it is an object of the invention to find a process for preparing cyclobutanone starting from cyclopropylmethanol which can be carried out with good space-time yield and also very low waste burden. In addition, a very simple scale-up and continuous process is possible.

It has now been found that, surprisingly, it is possible to obtain cyclobutanol in a process which is salt-free overall by isomerizing cyclopropylmethanol in the presence of a heterogeneous acidic catalyst, and that said cyclobutanol can be dehydrogenated to cyclobutanone over a heterogeneous catalyst. The present invention therefore provides a salt-free process for preparing cyclobutanone by isomerizing cyclopropyl-methanol to cyclobutanol in the presence of an acidic heterogeneous catalyst and subsequently dehydrogenating the cyclobutanol over a heterogeneous catalyst.

DESCRIPTION OF THE PREFERRED EMBODIMENTS

The isomerization of cyclopropylmethanol preferably takes place in a solvent, and water is a particularly preferred solvent. The cyclobutanol can be isolated from the aqueous mixture using common extractants without addition of salt. The cyclobutanol, preferably obtained after distillative removal of the extractant, can then be dehydrogenated to cyclobutanone over a heterogeneous catalyst without further purification and without addition of further reagents or solvent. The reaction effluent can optionally be purified by a thermal separating operation, preferably a distillation. The process can be carried out batchwise or continuously.

In the case where water is used as a solvent and the resulting reaction mixture is extracted, of recycling extractant and aqueous phase after the extractive workup results in hardly any wastewater and no salt. Apart from the by-products formed in the reaction, no wastes are produced by using assistants.

It has also been found that, surprisingly, the selectivity of the isomerization reaction in, for example, an aqueous medium, even when minimizing the water content in the cyclopropylmethanol/water reactant mixture, does not necessarily worsen. In fact, considerable improvements in the space-time yield can be achieved.

For the isomerization, heterogeneous acidic catalysts are used. In particular, acidic ion exchange resins and acidic clay minerals can be used. Examples of acidic ion exchange resins include crosslinked, sulfonated polystyrenes, for example LEWATIT S100® from BAYER AG. Examples of acidic clay minerals include acidic montmorillonites, for example KSF® and other K catalysts from Sudchemie AG.

The catalysts can either be contacted with the cyclopropylmethanol directly as a suspension in a stirred vessel or preferably in a continuous process in a cylindrical, heatable vessel as a catalyst bed through which reaction medium flows (fixed bed). A continuous variant can be performed as a continuously operated bypass reactor of a stirred tank or as a reactor in single or straight pass. Particular preference is given to continuous processes since a continuous process allows defined residence times which result in high selectivities.

The reaction is advantageously carried out at temperatures of 50–150° C., preferably at temperatures of 70–100° C., in particular at temperatures of 85–95° C. It is advantageous to preheat the catalyst bed to the preferred temperature range, and if at all possible no axial temperature gradient should occur in the catalyst bed as the feed mixture flows through. When preparing cyclobutanol, rapid cooling of the product stream after leaving the reaction zone is very important in order to achieve a very high selectivity and yield.

The heterogeneous acidic catalyst can be reused without any problem.

When the isomerization is carried out in an aqueous system, the ratio of cyclopropylmethanol to water can be varied within very wide limits. However, from an economic point of view and to optimize the space-time yield, it is advantageous to use very little water in the mixture. A ratio of water to cyclopropylmethanol of from 6:1 to 0.5:1 is therefore suitable. However, preference is given to using a ratio of water to cyclopropylmethanol of from 3:1 to 1.3:1.

In the preferred continuous method, it is possible to realize liquid hourly space velocities (LHSV) based on cyclopropylmethanol used of from 0.01 to 2 l of cyclopropylmethanol$\cdot h^{-1} \cdot l^{-1}$ of catalyst at optimum yield and selectivity. The preferred liquid hourly space velocity for the process is from 0.05 to 1 l of cyclopropylmethanol$\cdot h^{-1} \cdot l^{-1}$ of catalyst.

Cyclobutanol is formed once the reactant mixture has been fed to the reaction zone as a homogeneous mixture of water and cyclopropylmethanol. Since cyclobutanol does not have unlimited miscibility with water it partly separates from water as an organic phase. Since considerable amounts of cyclobutanol are dissolved in the aqueous phase, the biphasic product mixture is used directly in a subsequent extraction stage. The aqueous phase can also be recycled by feeding this mixture back to the reaction zone after charging with new cyclopropylmethanol.

The extraction of the desired product from the reaction mixture can be carried out by known extraction methods, preferably using customary extractants having a boiling point which differs markedly from the boiling point of the target product. The boiling points of the extractants are therefore preferably <100° C. or >130° C. Examples include ethers, for example diethyl ether, methyl tert-butyl ether, butyl ethyl ether and diisopropyl ether, esters, for example ethyl acetate and methyl acetate, aliphatic and cycloaliphatic hydrocarbons, for example pentane, hexane and cyclohexane, aromatic hydrocarbons, for example benzene and toluene, and halogenated hydro-carbons, for example dichloromethane and chloroform. However, the use of halogenated extractants is less preferred, since, if at all possible, no halogenated compounds should come into contact with the reaction medium.

As a consequence of the advantageous density differences of the desired product to water, it is not necessary to saturate the aqueous phase with salts before the extraction.

Particular preference is given to extraction with methyl tert-butyl ether (MTBE). Depending on the method, the crude cyclobutanol product obtained after removal of the extractant contains 50–70% of cyclobutanol, 5–10% of 3-buten-1-ol and also higher-boiling by-products. This mixture can either be worked up distillatively or preferably used directly in the subsequent dehydrogenation step. Distillation of the crude product can provide cyclobutanol in a purity of >95% which can be used as such. However, it has proven useful in practice to separate the distillation residue from high-boiling secondary components by distilling it over once, for example on a rotary evaporator or on a short-path distillation apparatus. In this way it is possible to achieve cyclobutanol purities of 70–80%.

Both the extractant and the aqueous phase can be reused without any problem.

Cyclobutanol is generally dehydrogenated to cyclo-butanone over a heterogeneous dehydrogenation catalyst, especially over a copper- and/or a chromium-containing catalyst. The catalyst can comprise metal oxides as promoters. The use of barium oxide or manganese oxide has proven especially useful. The catalysts can be used unsupported or, for example, in the presence of alumina or silica as support material.

As a consequence of the thermal instability of cyclobutanol and cyclobutanone and also the tendency of cyclobutanone to react further under oxidative conditions in a Bayer-Villiger oxidation to give γ-butyrolactone, the resulting successful reaction with good selectivity and yield at the high temperature is surprising. It is also surprising that the product mixture obtained in the first process step can be successfully used under the given reaction conditions (high temperatures, presence of an active catalyst).

Preference is given to carrying out the dehydrogenation in a gas phase reaction by passing crude cyclobutanol product which has been evaporated beforehand in a nitrogen stream over a fixed catalyst bed in a heated furnace. It is also possible to feed the crude cyclobutanol product dropwise directly onto the catalyst bed. Diluting with solvents is not necessary. After leaving the reaction zone, the product mixture is cooled and preferably fed directly to the distillation. Preceding workup is not necessary.

In an alternative process, the pulverulent catalyst is suspended in a high-boiling medium (for example white oil) and heated. The crude cyclobutanol product is then metered into the catalyst suspension via an immersed pipe and the product mixture formed is distilled off via a distillation head with condenser. This liquid phase process may be advantageous for apparatus reasons, since it can be carried out in a normal stirred tank, but is generally inferior to the gas phase process with regard to conversion and space-time yield.

The catalyst can be used directly in the reaction. Activation, for example with hydrogen, is not necessary. It is also unnecessary to mix the crude cyclobutanol product with hydrogen or steam for catalyst activation during the reaction. The catalyst can be reused.

The gas phase reaction is advantageously carried out at a temperature of from 180 to 350° C. In a preferred version, the dehydrogenation is carried out within a temperature range 220–280° C. The reaction is also advantageously carried out at atmospheric pressure or at a slight elevated pressure of preferably up to approx. 3 bar.

In the gas phase dehydrogenation, liquid hourly space velocities (LHSV) in the range of from 0.1 to 5.0 $l \cdot h^{-1} \cdot l^{-1}$ of catalyst (based on crude liquid cyclobutanol product) can be attained. In a preferred method, the liquid hourly space velocity is in the range from 0.2 to 4 $l \cdot h^{-1} \cdot l^{-1}$ of catalyst, and in a particularly preferred method, the liquid hourly space velocity is in the range from 0.3 to 3 $l \cdot h^{-1} \cdot l^{-1}$ of catalyst.

Depending on the composition of the starting material, the product mixture obtained in the dehydrogenation comprises preferably approx. 60–65% of cyclobutanone and also, depending on the completeness of the conversion, from 0 to about 10% of remaining cyclobutanol. The composition of the by-product spectrum changes only slightly relative to the composition of the by-products of the starting material. The 3-buten-1-ol by-produced in the isomerization is converted with high selectivity to butyraldehyde which can be efficiently removed by distillation. γ-Butyrolactone is only formed to a slight extent (<2%) in the dehydrogenation. In the dehydrogenation, yields up to 90% based on cyclobutanol used are achieved.

Distillation of the product mixture can provide cyclobutanone in a purity of >99%.

The process is also suitable for the preparation of alkyl-substituted cyclobutanones and also for the preparation of cyclic ketones having relatively large rings (for example cyclopentanone, cyclohexanone).

The starting material cyclopropylmethanol is obtainable, for example, by hydrogenation of methyl cyclopropanecarboxylate (DE-A-35 38 132) or cyclopropane-carbaldehyde (EP-A-0 794 166). Those portions of each of which are relevant to the preparation of cyclopropyl methanol are incorporated herein by reference.

EXAMPLES

The examples cited hereinbelow are intended to illustrate the invention without further limiting it.

Example 1

Recycle Method

A mixture of 100 g (1.4 mol) of cyclopropylmethanol and 370 g of deionized water was pumped from a reservoir (unheated) via a preheating zone (approx. 75° C.) from below through a heatable 0.5 m column which was filled with 216 g of LEWATIT S100® (H+ form) and 190 g of deionized water (rate approx. 300 ml/h). The temperature within the column was 90–95° C. After leaving the column, the reaction mixture was recycled to the reservoir. After approx. 8 hours of reaction time, the conversion wa greater than 99% and the reaction was ended. The reaction mixture was fully discharged from was column and then extracted with methyl tert-butyl ether (MTBE, approx. 360 g) in a perforator. After removing MTBE on a rotary evaporator, 87 g of rotation residue were obtained (cyclobutanol content: 70%, yield: 62%).

Example 2

Single Pass

A mixture of 100 g (1.4 mol) of cyclopropylmethanol and 280 g of deionized water was pumped (without preceding water addition) from a reservoir through the column filled with ion exchanger described in Example 1 (rate approx. 200 ml/h). The product mixture was removed at the top of the column and fed directly to extraction as described above. At the end of the reaction, a further 150 g of water was pumped in, in order to flush the column. The washing water was likewise fed to the extraction. After removal of MTBE, 83 g of residue were obtained on the rotary evaporator (cyclobutanol content: 70%, yield: 60%).

Example 3

Single Pass

A jacketed, cylindrical 9 l glass vessel was charged with 6.5 kg of LEWATIT S100® (H+ form) and bounded at both sides by frits. A cavity which was formed between the upper end of the catalyst bed and the lower end of the glass vessel was charged with glass beads in order to reduce the excess volume. The catalyst bed was heated from outside through the jacket with the aid of a heat carrier liquid (silicone oil) (temperature in the catalyst bed 90–95° C.). A mixture of 1.5 kg of cyclopropylmethanol (20.85 mol) and 4.2 kg of water was passed from below through the catalyst bed at a rate of 2 kg/h. The product mixture was removed at the upper end of the reaction vessel and was extracted with MTBE (4×3.6 kg). The combined organic phases were concentrated on a rotary evaporator. 1.24 kg of crude cyclobutanol were obtained (cyclobutanol content: 63%, yield: 51%).

Example 4

Single Pass

In the apparatus described in Example 3, a mixture of 1.5 kg (20.85 mol) of cyclopropylmethanol and 2.1 kg of water was reacted (pumping rate: 2 kg/h). The product mixture obtained was extracted with MTBE (3×3.0 kg) and the combined organic phases were concentrated on a rotary evaporator. 1.21 kg of crude cyclobutanol were obtained (cyclobutanol content: 60%, yield: 49%).

Example 5

Liquid Phase Dehydrogenation

A suspension of 10 g of catalyst (Cu-0202 P from Engelhard, comprises 67% by weight of Cu and 12% by weight of Cr) in 90 g of paraffin oil was heated to 160° C. in a 250 ml reaction flask equipped with a distillation head with condenser. 108 g of crude cyclobutanol product (purity: 73%, 1.14 mol) were metered into the bottoms via a dropping funnel with inlet tube and distillate removed at the same time via the distillation head with condenser. The collected distillates were analyzed by gas chromatography and then passed again through the catalyst bottoms. After four passes, 92 g of distillate were obtained having an average cyclobutanone content of 73% and a remaining cyclobutanol content of 13% (conversion: 85%, selectivity >98%).

Example 6

Gas Phase Dehydrogenation

A quartz glass tube charged with 50 g of catalyst (H1044, composition approx. 27 g of copper oxide, approx. 4 g of chromium oxide, approx. 5 g of barium oxide, on $SiO_2$) and bounded at both ends with Raschig rings was installed in a commercial, electrically heated laboratory tubular furnace and the temperature in the catalyst zone was set to 200° C. 30 g of crude cyclobutanol product (purity approx. 73%, 0.3 mol) were evaporated using a preevaporator and then passed over the catalyst (LHSV=0.18/h). After leaving the catalyst zone, the reaction mixture was cooled using a condenser and collected in a cold trap. 27 g of reaction effluent were obtained, having a composition of 59% of cyclobutanone and 19% of cyclobutanol (conversion: 77%, selectivity: 96%).

Example 7

Gas Phase Dehydrogenation

In the experimental apparatus described in Example 6 (same catalyst), 256 g of crude cyclobutanol (purity approx. 74%) were converted at 250° C. (LHSV=0.33/h). 243 g of reaction effluent were obtained having an average composition of 63% of cyclobutanone and 12% of cyclobutanol (conversion: 84%, selectivity >98%). Distillation of the product mixture through a 1 m Multifil column provided 102 g of cyclobutanone in a purity of >99% (b.p.: 97–99° C., distillation yield: 67%).

Example 8

Gas Phase Dehydrogenation

The quartz glass tube was filled with 50 g of catalyst (H1044, calcined at 700° C.) and was stored in the laboratory tubular furnace as in Example 7. Likewise as described, 135 g (1.3 mol) of crude cyclobutanol (purity 71%) were passed over the catalyst at 250° C. (LHSV= 0.33/h). 127 g of reaction effluent were obtained having an average composition of 58% of cyclobutanone and 2.5% of cyclobutanol (conversion: 97%, selectivity: 82%).

Example 9

Gas Phase Dehydrogenation

The quartz glass tube was filled with 50 g of catalyst (H1044, calcined at 650° C.) and stored in the laboratory tubular furnace as described in Example 7. 776 g of crude cyclobutanol (purity: 71%) were then passed in gaseous form over the catalyst at 250° C. (LHSV=0.33/h). 719 g of reaction effluent were obtained having an average composition of 67% of cyclobutanone and 5% of cyclobutanol (conversion: 94%, selectivity: 97%). Distillation of the product mixture through a 1 m Multifil column resulted in 380 g of cyclobutanone (purity >95%, distillation yield 81%).

Example 10

Gas Phase Dehydrogenation

The quartz glass tube was filled with 50 g of catalyst (H1044, calcined at 650° C.) and stored in the laboratory tubular furnace as described in Example 7. 876 g of crude cyclobutanol (purity: 75%) were then passed in gaseous form over the catalyst at 250° C. (LHSV=1.5 h$^{-1}$). 832 g of reaction effluent were obtained having an average composition of 67% of cyclobutanone and 8% of cyclobutanol (conversion: 90%, selectivity: 97%). Distillation of the product mixture through a 1 m Multifil column resulted in 516 g of cyclobutanone (purity >95%, distillation yield 80%).

German application DE 10162456.5 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

What is claimed is:

1. A process which comprises
isomerizing cyclopropylmethanol to cyclobutanol in the presence of an acidic heterogeneous catalyst and subsequently
dehydrogenating the cyclobutanol over a heterogeneous dehydrogenation catalyst to form cyclobutanone.

2. The process as claimed in claim 1, wherein the cyclopropylmethanol is present as a mixture with water and the cyclobutanol formed by isomerization is an aqueous mixture.

3. The process as claimed in claim 2, further comprising extracting the aqueous mixture to form an extract comprising cyclobutanol before dehydrogenating.

4. The process as claimed in claim 1, wherein the acidic heterogeneous catalyst is a fixed bed catalyst.

5. The process as claimed in claim 1, wherein the acidic heterogeneous catalyst is present in the form of a suspension.

6. The process as claimed in claim 1, wherein the acidic heterogeneous catalyst is an acidic ion exchanger.

7. The process as claimed in claim 6, wherein the ion exchanger is a crosslinked polystyrene having sulfonic acid groups.

8. The process as claimed in claim 7, wherein the cyclopropylmethanol is present as a mixture with water, and said mixture is isomerized by passing said mixture in a single pass through a bed of acidic ion exchangers having sulfonic acid groups.

9. The process as claimed in claim 1, wherein the isomerization is carried out at 50–150° C.

10. The process as claimed in claim 1, wherein the isomerization is carried out at 70–100° C.

11. The process as claimed in claim 1, wherein the liquid hourly space velocity in the isomerization is from 0.01 to 2 l of cyclopropylmethanol·h$^{-1}$·l$^{-1}$ of catalyst.

12. The process as claimed in claim 2, wherein the ratio of water to cyclopropylmethanol in the mixture is from 6:1 to 0.5:1.

13. The process as claimed in claim 2, wherein the ratio of water to cyclopropylmethanol in the mixture is from 3:1 to 1.3:1.

14. The process as claimed in claim 1, wherein the dehydrogenation is carried out in a gas phase reaction by contacting the cyclobutanol with the heterogeneous dehydrogenation catalyst in a single pass, said process further comprising
distilling the cyclobutanone without further workup.

15. The process as claimed in claim 1, wherein the dehydrogenation is carried out in a suspension in a high-boiling medium in the presence of a pulverulent catalyst.

16. The process as claimed in claim 1, wherein the heterogeneous dehydrogenation catalyst comprises copper and chromium.

17. The process as claimed in claim 1, wherein the dehydrogenation is carried out in the gas phase at a temperature of 180–350° C.

18. The process as claimed in claim 1, wherein the dehydrogenation is carried out in the gas phase at a temperature of 220–280° C.

19. The process as claimed in claim 1, wherein the liquid hourly space velocity in the hydrogenation is from 0.1 to 5 l·h$^{-1}$·l$^{-1}$ of catalyst.

20. The process as claimed in claim 1, carried out in the absence of any added salt.

* * * * *